Figure 1:
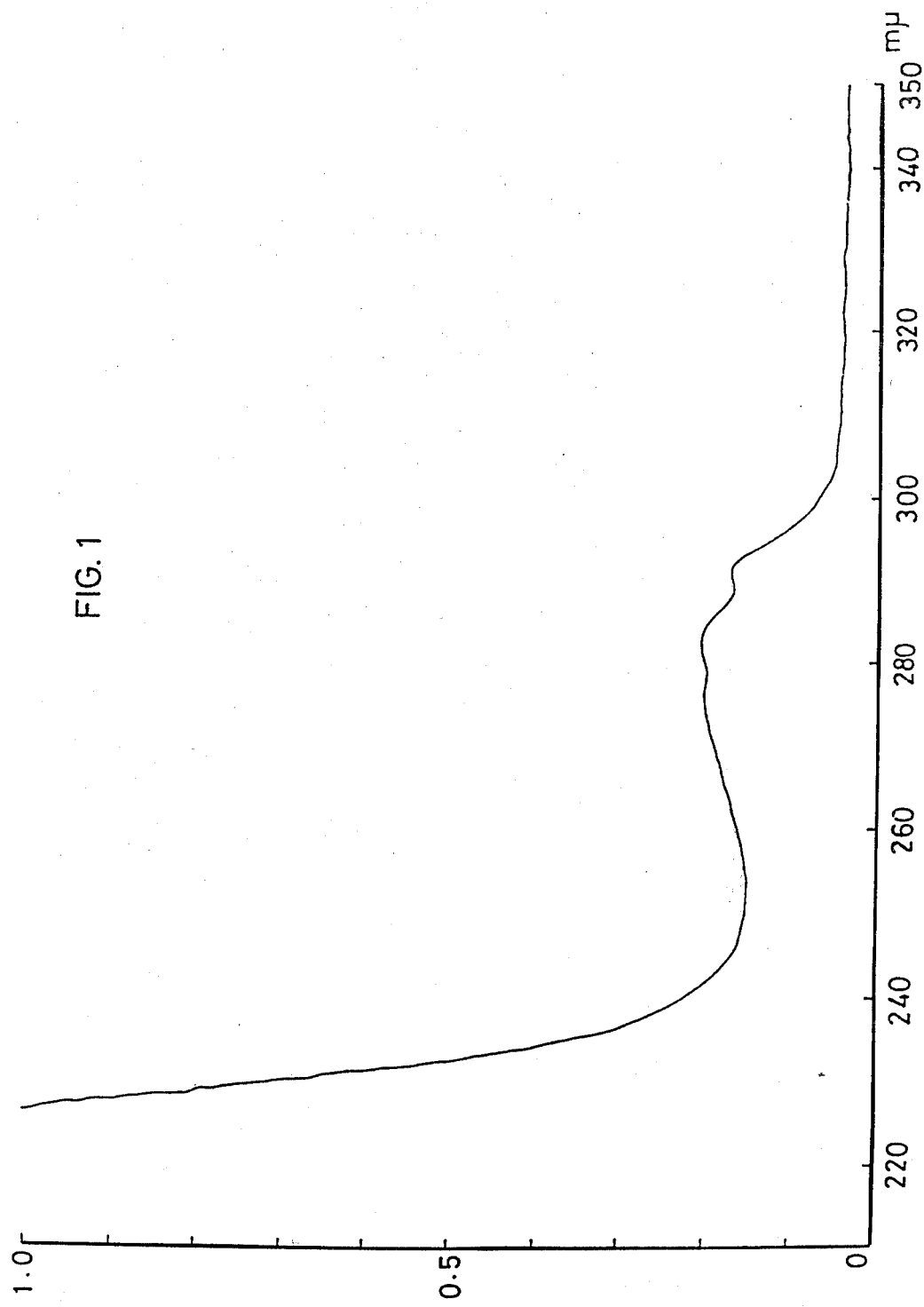

United States Patent [19]

Umezawa et al.

[11] 4,393,047
[45] Jul. 12, 1983

[54] ANTIBIOTIC CYTOPHAGIN AND A PROCESS FOR PRODUCING THE SAME

[75] Inventors: Hamao Umezawa; Tomio Takeuchi, both of Tokyo; Hiroshi Nakano, Machida, all of Japan

[73] Assignee: Microbiochemical Research Foundation, Tokyo, Japan

[21] Appl. No.: 279,489

[22] Filed: Jul. 1, 1981

Related U.S. Application Data

[63] Continuation-in-part of Ser. No. 131,344, Mar. 18, 1980, abandoned.

[51] Int. Cl.³ .................. A61K 35/00; C12P 1/04; C12P 21/00; C12R 1/01
[52] U.S. Cl. .................. 424/118; 435/170; 435/68; 435/822
[58] Field of Search .................. 435/170, 68; 424/118

[56] References Cited

PUBLICATIONS

Lewin et al., J. Gen. Microbiol., vol 58, pp. 145–170 (1969).

Primary Examiner—Alvin E. Tanenholtz
Attorney, Agent, or Firm—Wolder, Gross & Yavner

[57] ABSTRACT

A substance having antibiotic activity, designated as cytophagin, which is stable in the form of colorless powder and which has an elemental analysis of H: 6.94%, C: 47.22% and N: 13.21%, a molecular weight of 1,000 to 1500. This substance is believed to be composed of 11 amino acids and exhibits a strong activity against Gram-positive bacteria. Cytophagin is produced by fermentation using a microorganism belonging to the genus Cytophaga and capable of producing cytophagin. A preferred strain is Cytophaga BMF 694-N3 (FERM P-4846;NRRL B-12109). Cytophagin is of potential interest as medicament or veterinary agent because of its antibiotic activity.

4 Claims, 2 Drawing Figures

ANTIBIOTIC CYTOPHAGIN AND A PROCESS FOR PRODUCING THE SAME

RELATED APPLICATION

The present application is a continuation-in-part of our copending application Ser. No. 131,344 filed Mar. 18, 1980 and now abandoned.

SUMMARY OF THE INVENTION

This invention relates to a new antibiotic designated by us as cytophagin and a process for producing the same. This invention is based upon the discovery that a certain microorganism belonging to the genus Cytophaga and variants thereof are capable of producing a new antibiotic substance which is particularly active against various Gram-positive bacteria. A preferable microorganism capable of producing such an antibiotic substance, designated by us as cytophagin, has been isolated by us from the soil of Kotomizuen-suijo, Gifu-ken, Japan.

Thus, this invention is directed to provide a new antobiotic designated as cytophagin and a process for producing the same.

According to this invention, there is provided an antibiotic referred to as cytophagin and having the following physico-chemical properties:

(1) Elemental analysis: H: 6.94%, C: 47.22%, N: 13.21%

(2) Molecular weight: 1,000 to 1,500 [determined by gel filtration using Sephadex LH20 (commercial product of Pharmacia Fine Chemicals AB., Sweden)]. 1,380 [calculated from the $OD_{280}$ value of tryptophane and also supported by the results of amino acids analysis].

(3) Melting point: Browning at about 210° C. Decomposition with foaming at about 220° C.

(4) Specific rotation: $[\alpha]_D^{25} = +5°$ (c=1 in DMSO)

(5) Ultraviolet absorption spectrum: As shown in FIG. 1 (c=25 μg/ml in methanol).

Figure 2:
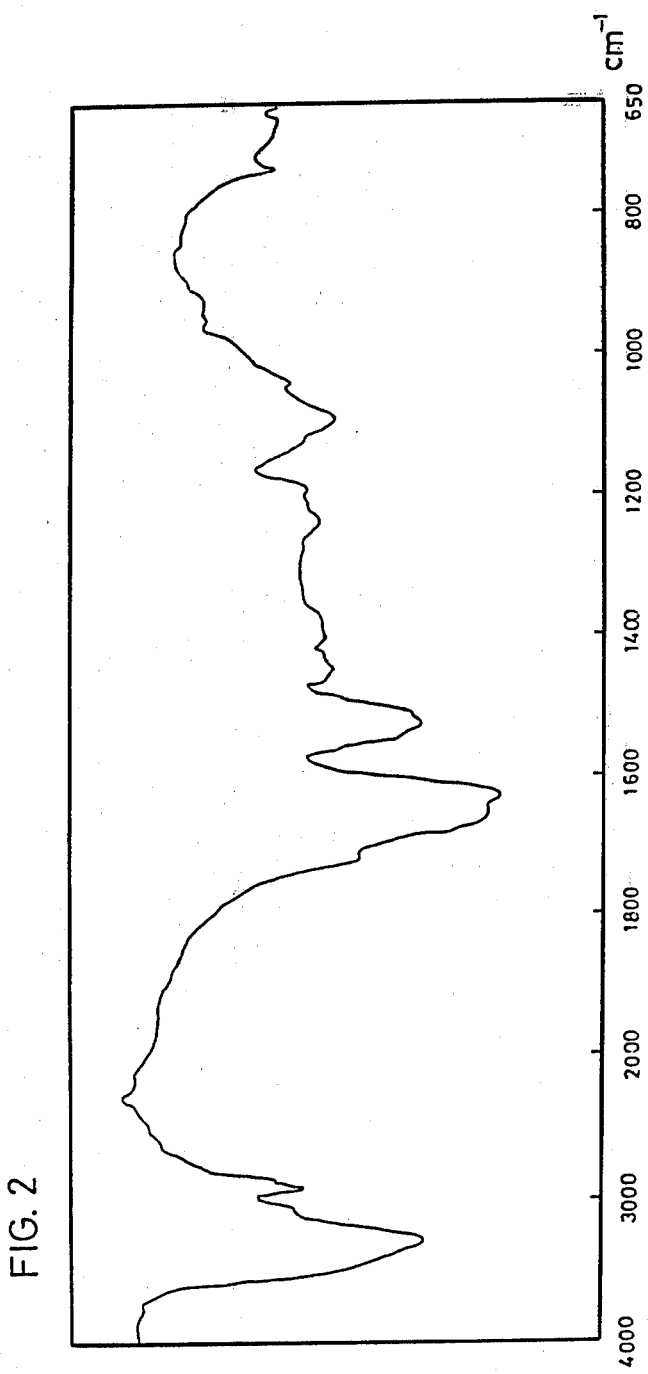

(6) Infrared absorption spectrum: As shown in FIG. 2 (by KBr tablet method)

(7) Solubility in various solvents: Readily soluble in acetic acid and dimethylsulfoxide, substantially soluble in methanol and ethanol, and hardly soluble in water, chloroform, acetone, ethyl acetate and ethyl ether.

(8) Color reaction: Positive in ninhydrin reaction, Ehrlich reaction and isatin reaction, and negative in Sakaguchi reaction, Pauly reaction and anisidine reaction.

(9) Nature: Showing the behavior of neutral substance by a filter paper electrophoresis.

(10) Color and appearance: Colorless powder

(11) Amino acid compositipon: By decomposition with 3 N methanesulfonic acid at a temperature of 110° C. for 24 hours, followed by analysis using an amino acids analyzer the following amino acids were found: lysine, aspartic acid, threonine, serine, proline, glycine, leucine and tryptophane.

By ninhydrin reaction, 3 positive substances were found, which are not yet identified and suspected to be amino acids.

With respect to the relationship of the molecular weight and amino acids constituents, the substance of this invention is considered to contain each one molecule of these amino acids.

(12) Rf value: 0.23 [by silica gel thin layer chromatography using Silica gel plate Art. 5721 (commercial product of Merck Ag., Germany) and a solvent system of n-butanol/acetic acid/water (12:3:5 by volume)]

The antibiotic of this invention possesses the following biological properties.

The minimum growth inhibitory concentrations of cytophagin against various microorganims are shown in the following Table 1.

TABLE 1

| Microorganisms tested | MIC (μg/ml)** |
|---|---|
| Staphylococcus aureus FDA 209P | 1.56 |
| Staphylococcus aureus MS 8800 [resistant to penicillin, tetracyclin, streptomycin and erythromycin] | 1.56 |
| Staphylococcus sp M-XX-0105 [resistant to amikacin, tobramycin and DKB] | 2.5 |
| Sarcina lutea PCI 1001 | 0.1 |
| Bacillus subtilis NRRL B-558 | 1.56 |
| Bacillus subtilis PCI 219 | 1.56 |
| Micrococcus lysodeikticus IFO 3333 | 0.1 |
| Escherichia coli K-12 | >100 |
| Pseudomonas aeruginosa A 3 | >100 |
| Mycobacterium smegmatis ATCC 607 | >100 |
| Candida albicans 3147 | 50 |

**Determined by agar dilution method using a bouilon medium (pH:7).

As is apparent from Table 1, cytophagin in strongly active against the growth of various Gram-positive bacteria.

The acute toxicity of cytophagin was determined by using mouse as test animals. All of them (two groups, each consisting of 3 mouse) survived after administration (ip.) of 200 mg/kg of cytophagin dissolved in DMSO/water.

Thus, cytophagin is of potential interest as medicament and veterinary agent owing to its high antibiotic activity.

From the above-mentioned properties, cytophagin is ascertained as a substance composed of 11 amino acids. Although various other antibiotic substances originating from bacteria or actinomycetes are know in the art, all of them are different from cytophagin with respect to the amino acid composition. Thus it has been ascertained as a new antibiotic substance.

According to another feature of this invention, there is provided a process for producing cytophagin by fermentation, characterized by culturing a microorganism belonging to the genus Cytophaga and capable of producing cytophagin in a culture medium, accumulating cytophagin in the cultured broths and recovering cytophagin therefrom.

A preferred example of the microorganisms which may be used in the process of this invention is Cytophaga BMF 694-N3 (Deposition Number of Biseibutus Kogyo Kenkyusho, Japan: FERM P-4846) (also NRRL B-12109, U.S. Department of Agriculture, Peoria, Ill.) used in the following example, although it is possible to use any suitable mutant strain thereof may be used.

The mycological characteristics of Cytophaga BMF 694-N3 (FERM P-4846; NRRL B-12109) are as follows.

(I) Morphological characteristics: When cultured by using a bouillon-agar medium, the cells are bacilliform of 0.2–0.4×1.2–12 microns. Motile by gliding. No flagella. No spore formation. No pleomorphism.

(II) Culturing characteristics:

(1) Bouillon-agar culture; Colonial morphology is remarkably affected by the concentrations of the nutrients. By using a rich nutrient agar medium such as for example one using a usual bouillon containing 1% peptone, colonies are raised and convex and take the form of from trapezoid to hemisphere having an entire edge. By using a poor nutrient medium such as for example an agar medium containing 0.2% peptone, colonies are flat and their edges are thin and spreaded by gliding. Cells are yellowish.
(2) Bouillon culture: Turbid throughout the entire medium, and highly turbid in the near of the liquid surface.
(3) Bouillon-gelatin stab culture: From the liquid surface, gradually liquified.
(4) Milk culture: Unchanged (III) Physiological characteristics:
(1) Reduction of nitrate: negative
(2) Denitrogen reaction: negative
(3) MR test: negative
(4) VP test: negative
(5) Formation of indole: negative
(6) Formation of hydrogen sulfide: negative
(7) Hydrolysis of starch: positive
(8) Utilization of citric acid: positive
(9) Utilization of inorganic nitrogen source: As a sole nitrogen source, ammonium salt is utilized.
(10) Formation of pigment: Forming yellowish, water-insoluble pigment
(11) Urease: negative
(12) Oxidase: negative
(13) Catalase: negative
(14) Range of growing conditions: PH 6 to 10. Below 35° C., preferably 15° to 30° C.
(15) Behaviour to oxygen: anaerobic
(16) C-F test: Slowly forming acids, regardless to the presence of paraffin seal.
(17) Utilization of sugars:
Utilized:
Glucose, fructose, sucrose, maltose, lactose, mannose, trehalose, dextrin and starch
Not utilized:
Galactose, xylose, arabonose, sorbit, mannit, inosit and gylcerin.

The above-mentioned microbiological characteristics have been investigated with reference to Bergey's Manual of Determinative Bacteriology, 8th edition (1974) to give the following result.

This strain is a Gram-negative microorganims and in the bacilliform having irregular length. It has no branch, helix and sheath. The colonies are yellowish on agar medium, and the colonies on poor nutrient agar medium form thin, spreading edges owing to gliding. From these characteristics, this strain has been identified as one belonging to the genus Cytophaga.

The microorganisms which may be used for the production of cytophagin according to this invention may be cultured by using any and all media which may be used for conventional fermentation techniques.

For instance, glucose, dextrin, sucrose, maltose and the like may be used as the carbon source, and peptone, corn steep liquor, soybean meal, ammonium sulfate and the like may be used as the nitrogen source. Also, suitable inorganic salts such as for example, sodium chloride, calcium carbonate and the like may be added to the medium. It is also possible, if desired, to add a suitable defoaming agent to the medium.

For fermentation, any method using a liquid medium (e.g. shaking-culturing, submerged culturing with aeration and agitation and the like) is preferable. The fermentation temperature may be, for example, from 10° to 35° C. and the fermentation period may preferably be 2 to 5 days. In this manner, a large amount of cytophagin is accumulated mainly in the cultured broths.

In order to determine cytophagin, for example, any usual agar medium is used as the culture medium and *Staphylococcus aureus* 209P or *Bacillus subtilis* PCI 219 is used as the determinative strain.

With respect to the above-mentioned physico-chemical characteristics, it is possible to extract and purify cytophagin by using various methods which may conventionally be applied to the extraction and purification of substances having such characteristics, as exemplified in the following.

When a cultured liquor containing the active substance is passed through a column packed with Amberlite XAD-2 (commercial product of Rohm and Haas Co., U.S.A.), the active substance is adsorbed onto the resin. The column is washed with deionized water and/or 50% methanol water, and then the active substance is eluted with 50% propanol. The eluate is collected and concentrated to give a precipitate. The precipitate is dissolved in acetic acid and the solution is added with ethyl acetate to result in a precipitate containing the active substance, which is collected and concentrated to dryness under reduced pressure to obtain a crude product of cytophagin. For further purification of the crude product, chromatography using a suitable ion exchanger or agent for gel filtration, butanol extraction and precipitation method and the like may be used solely or in combination.

DRAWINGS

FIGS. 1 and 2 show the ultraviolet absorption spectrum and infrared absorption spectrum of cytophagin of this invention.

PREFERRED EMBODIMENTS the following non-limiting examples illustrate the invention.

EXAMPLE 1

Each 100 ml of a liquid medium containing galactose (2%), dextrin (2%), Bacto-Soyton (Difco; 1%), corn steep liquor (0.5%), ammonium sulfate (0.2%) and a silicon defoaming agent (0.03%) was put into each of 80 Erlenmeyer flasks (capacity: 500 ml) which were then sealed with cotton plugs. The media were sterilized at 120° C. for 15 minutes under pressure and inoculated with a seed of Cytophaga BMF 694-N3 (FERM P-4846; NRRL B-12109) which had been prepared by using a similar medium. The fermentation was effected at 30° C. for 4 days to obtain cultured broths (6 l in total; pH 7.0) containing cytophagin (50 μg/ml). The supernatant was passed through a column packed with Amberlite XAD-2 (one l; commercial product of Rohm and Haas Co., U.S.A.) to adsorb the active substance onto the resin. After washing the column with water (5 l) and subsequently with a mixture of methanol and water (1:1, 10 l), the elution was effected by using a mixture of propanol and water (1:1, 5 l). The effluent was divided into fracions (each 200 ml), and Fraction Nos. 2 to 20 were collected and combined, and the combined fractions were concentrated under reduced pressure to obtain a precipitate containing the active substance. The precipitate was dissolved in acetic acid (50 ml) which was filtered to remove insoluble substances from the filtrate, to which ethyl acetate (500 ml) was added to give a precipitate. This precipitate was dissolved in acetic acid (50 ml), and the solution was added with water (500 ml) and butanol (500 ml). By shaking the mixture, the active substance is transferred to n-butanol phase. The aqueous phase was further extracted twice with n-butanol (each 500 ml). The n-butanol extracts were combined and concentrated to dryness under reduced pressure. The dried substance was dissolved in acetic acid (20 ml) and then added with ethyl acetate (200 ml) to give a precipitate which was collected by centrifugation (6000 r.p.m. for 20 minutes) and concentrated to dryness under reduced pressure. There was obtained a final product of cytophagin (35 mg; purity about 90%). Its physico-chemical properties are hereinbefore described.

EXAMPLE 2

Each 110 ml of a culture medium containing dextrin (2%), sucrose (2%), soybean meal (1%), corn steep liquor (0.5%), ammonium sulfate (0.2%), potassium chloride (1%) and a silicon defoaming agent (0.03%) was put into each of 70 Erlenmeyer flasks (capacity: 500 ml) and sterilized at 120° C. for 15 minutes under reduced pressure. A seed of Cytophaga BMF 694-N3 (NRRL B-12109) which had been prepared by using a similar medium was inoculated onto each of the media, and the fermentation was effected with shaking at 28° C. for 4 days to obtain cultured broths (5 liter; pH 7.7) containing cytophagin 120 μg/ml). The supernatant was passed through a column packed with Amberlite XAD-2 (one l; commercial product of Rohm and Haas Co., U.S.A.) to adsorb the active substance onto the resin. After washing the column with water (5 l) and subsequently with a mixture of methanol and water (1:1, 10 l), the elution was effected by using a mixture of MeOH, water and acetic acid (1:1:0.1). The effluent was divided into fractions (each 200 ml) and Fraction Nos. 2 to 15 were collected and combined, and the combined fractions were concentrated under reduced pressure to obtain an oily substance which was added with dimethylsulfoxide (20 ml) to remove insoluble substances. The supernatant was added with a mixture of methanol and water (1:1, 200 ml) and its pH was adjusted to 6.0 by using caustic sida. The solution was then passed through a column packed with DEAE-Sepharose CL (200 ml; commercial product of Pharmacia Fine Chemicals AB., Sweden) and filled with a mixture of methanol and water (1:1). The active substance was not adsorbed onto the resin but were passed through the column. The effluent was concentrated under reduced pressure and freeze-dried. The dried substance was dissolved in acetic acid (10 ml) which was then passed through a column packed with Sephadex LH 20 (100 ml; commercial product of Pharmacia Fine Chemicals AB., Sweden) and filled with a mixture of methanol, water and acetic acid (1:1:0.2). The elution was effected by using a solution of the same composition. The effluent was divided into fractions (each 15 ml) and Fraction Nos. 16 to 20 were collected and combined. The combined fractions were concentrated to dryness under reduced pressure. The dried substance was dissolved in acetic acid (5 ml), followed by addition of ethyl acetate (50 ml) to give a precipitate which was collected by centrifugation (600 r.p.m.) and dried up under reduced pressure to obtain a final product of cytophagin (44 mg; purity 95%). The physico-chemical properties of this product were substantially the same as the product of Example 1.

What is claimed is:

1. A substance having antibiotic activity, designated as cytophagin, which is stable in the form of colorless powder and which possesses the following physico-chemical properties:
   (1) Elemental analysis: H: 6.94%, C: 47.22%, N: 13.21%
   (2) Molecular weight: 1,000 to 1,500 [determined by gel filtration]
   (3) Melting point: Browning at about 210° C. and decomposing with foaming at about 220° C.
   (4) Specific rotation: $[\alpha]_D^{25} = +5°$ (c=1 in DMSO)
   (5) Ultraviolet absorption spectrum: As shown in FIG. 1 (c=25 μg/ml in methanol)
   (6) Infrared absorption spectrum: As shown in FIG. 2 (by KBr tablet method)
   (7) Solubility invarious solvents: Readily soluble in acetic acid and dimethylsulfoxide, substantially soluble in methanol and ethanol, and hardly soluble in water, chlorofoem, acetone, ethyl acetate and ethyl ether
   (8) Color reaction: Positive in ninhydrin reaction, Ehrlich reaction and isatine reaction, and negative in Sakaguchi reaction, Pauly reaction and anisidine reaction.
   (9) Nature: Neutral
   (10) Color and appearance: Colorless powder
   (11) Amino acids constituents: Lysine, aspartic acid, threonine, serine, proline, glycine, leucine, trypsine and other 3 amino acids (each one molecule thereof)
   (12) Rf value: 0.23 [by silica gel thin layer chromatography using as silica gel plate Art. 5721 (Merck AG., Germany) and a solvent system of n-butanol-/acetic acid/water (12:3:5)].

2. The substance of claim 1, in which the molecular weight is 1,380 [calculated from the $OD_{280}$ value of trypsine].

3. A process for producing the substance claimed in claim 1, which process comprises the steps of culturing a microorganism selected from Cytophaga BMF 694-N3 (FERM P-4846; NRRL B-12109) and mutants thereof capable of producing the said substance in a culture medium under aerobic conditions to accumulate the said substance in the cultured broths and recovering the said substance therefrom.

4. The process of claim 3, in which the culturing is effected at a temperature of from 10° to 35° C. for 2 to 5 days.

* * * * *